US010246405B2

(12) United States Patent
Ahn et al.

(10) Patent No.: US 10,246,405 B2
(45) Date of Patent: Apr. 2, 2019

(54) POROUS DIACETYLENE PARTICLES, SYNTHESIS METHOD THEREOF

(71) Applicant: Korea University Research and Business Foundation, Seoul (KR)

(72) Inventors: Dong June Ahn, Seoul (KR); Doo Ho Yang, Seoul (KR)

(73) Assignee: Korea University Research and Business Foundation, Seoul (KR)

( * ) Notice: Subject to any disclaimer, the term of this patent is extended or adjusted under 35 U.S.C. 154(b) by 368 days.

(21) Appl. No.: 15/008,167

(22) Filed: Jan. 27, 2016

(65) Prior Publication Data
US 2016/0137586 A1 May 19, 2016

Related U.S. Application Data

(62) Division of application No. 13/441,214, filed on Apr. 6, 2012.

(30) Foreign Application Priority Data

Jun. 7, 2011 (KR) .................. 10-2011-0054777

(51) Int. Cl.
*B01J 19/10* (2006.01)
*B82Y 30/00* (2011.01)
*B82Y 40/00* (2011.01)
*C07C 51/41* (2006.01)
*C07C 209/00* (2006.01)

(52) U.S. Cl.
CPC ............. *C07C 209/00* (2013.01); *B01J 19/10* (2013.01); *B82Y 30/00* (2013.01); *B82Y 40/00* (2013.01); *C07C 51/412* (2013.01); *B01J 2219/0877* (2013.01); *Y10T 428/2982* (2015.01)

(58) Field of Classification Search
None
See application file for complete search history.

(56) References Cited

U.S. PATENT DOCUMENTS 4,814,404 A * 3/1989 Matsuda ................. C08F 38/00
522/176

* cited by examiner

*Primary Examiner* — Amy C Bonaparte
(74) *Attorney, Agent, or Firm* — Mintz Levin Cohn Ferris Glovsky and Popeo, P.C.; Kongsik Kim (57) ABSTRACT

Provided are a radial porous diacetylene particle, which is synthesized by ion-bonding a diacetylene-containing dicarboxylic acid or diamine monomer represented by Formula 1 with a diamine or dicarboxylic acid monomer represented by Formula 2, and a method of manufacturing the same.

8 Claims, 10 Drawing Sheets

POROUS DIACETYLENE PARTICLES, SYNTHESIS METHOD THEREOF

CROSS REFERENCE TO RELATED APPLICATION

This is a divisional application of U.S. application Ser. No. 13/441,214 filed on Apr. 6, 2012, which claims priority to Korean Application No. 10-2011-0054777 filed Jun. 7, 2011. The applications are incorporated herein by reference

BACKGROUND OF THE INVENTION

1. Technical Field

The present invention relates to a porous diacetylene particle, and, more particularly, to a method of synthesizing a novel porous diacetylene particle having optical characteristics using a diacetylene-containing dicarboxylic acid or diamine monomer and a diamine or dicarboxylic acid monomer.

2. Description of the Related Art

Generally, a sensor material used in a biosensor requires high selectivity and sensitivity to a target material to be detected. For this reason, an enzyme and an antibody have been generally used as a matrix of a biosensor, but they are disadvantageous in that stability becomes poor when they are fixed in the biosensor, and in that they are expensive. Therefore, research into synthetic biosensors imitating the function of a biomaterial such as an enzyme or an antibody has been actively conducted. Polydiacetylene (PDA), which is an organic material used in such a biosensor, is generally used to detect chemical and biological materials because it has specific color characteristics.

Polydiacetylene (PDA) is a conjugate polymer, and is receiving considerable attention in several viewpoints. First, polydiacetylene (PDA) is generally prepared by irradiating self-assembled diacetylene supermolecules with UV. Second, when PDA is prepared under an optimum condition, it has a dark blue color having a maximum absorption wavelength of 640 nm. Third, blue PDA is changed into red PDA (maximum absorption wavelength of 550 nm) depending on environmental stimuli. Owing to the change of blue PDA into red PDA, various chemical sensors based on PDA have been developed. Therefore, it was reported that, since polydiacetylene (PDA) is optically characterized in that its color is changed depending on heat, Ph, physical or chemical stimuli or molecular recognition, it is used to detect the colors of biologically, chemically and environmentally important target materials such as DNA, viruses, proteins, metal ions, organic solvents, etc.

As a conventional polydiacetylene sensor, a sensor having a vesicle structure in which a film and a vesicle solution are fixed on a substrate has been used. This vesicle-type sensor is problematic in that the time required to detect a target material is not short and the accuracy required to detect the target material is not high because its fluorescent intensity is not high and the target material is not easily diffused. Further, the vesicle-type sensor is problematic in that samples must be treated cautiously because it is sensitive to thermal stimuli.

In the present invention, porous particles having a large surface area were prepared such that the diffusion efficiency of a target material to be detected is increased and the time required to detect the target material is decreased, and new monomers were introduced such that the fluorescent intensity of a sensor is improved and the sensor is not sensitive to thermal stimuli.

SUMMARY OF THE INVENTION

Accordingly, the present invention has been devised to solve the above-mentioned problems, and an object of the present invention is to provide a radial porous diacetylene particle and a method of synthesizing a radial porous diacetylene particle having optical characteristics using a diacetylene-containing dicarboxylic acid or diamine monomer and a diamine or dicarboxylic acid monomer.

In order to accomplish the above object, the present invention provides a radial porous diacetylene particle, which is synthesized by ion-bonding a diacetylene-containing dicarboxylic acid or diamine monomer with a diamine or dicarboxylic acid monomer.

BRIEF DESCRIPTION OF THE DRAWINGS

The above and other objects, features and advantages of the present invention will be more clearly understood from the following detailed description taken in conjunction with the accompanying drawings, in which.

DESCRIPTION OF THE PREFERRED EMBODIMENTS

Hereinafter, preferred embodiments of the present invention will be described in detail with reference to the attached drawings.

The present invention provides a radial porous diacetylene particle, which is synthesized by ion-bonding a diacetylene-containing dicarboxylic acid or diamine monomer represented by Formula 1 below with a diamine or dicarboxylic acid monomer represented by Formula 2 below:

$$G\text{-}(A)_x\text{-}C\equiv C\text{---}C\equiv C\text{---}(B)_y\text{-}G \quad \text{[Formula 1]}$$

wherein A and B are each independently selected from a substituted or unsubstituted alkyl group of two or more carbon atoms, an ethylene oxide group, an amide group and an ester group, G is selected from COOH and $NH_2$, and x and y are each independently an integer of 1 to 20, $$Q\text{-}(D)_m\text{-}Z\text{-}(E)_n\text{-}Q \quad \text{[Formula 2]}$$

wherein Z is selected from a substituted or unsubstituted alkyl group of one or more carbon atoms, a benzene group, a cycloalkyl group, a pyridine group, a pyrimidine group and a naphthalene group, D and E are each independently selected from a substituted or unsubstituted alkyl group of one or more carbon atoms, a benzene group, a cycloalkyl group, a pyridine group, a pyrimidine group and a naphthalene group, D, E and Z are different from each other, Q is selected from COOH and $NH_2$, m and n are each independently an integer of 0 to 20, and G of Formula 1 above is different from Q of Formula 2 above.

The diacetylene-containing dicarboxylic acid or diamine monomers having both hydrophilic and hydrophobic property can be formed into various types of Supramolecule (Langmuir-Blodgett film, Langmuir-Schafer film, Lamellar film, vesicle solution, vesicle fixed on substrate, etc.) by self assembly. When the diacetylene-containing dicarboxylic acid or diamine monomers are spaced apart from each other at regular intervals, they are exposed to UV (254 nm) to be polymerized, have a blue color, and do not reveal a fluorescence. The reason why polydiacetylene has a blue color is because π electrons in the main chain thereof absorb light having a wavelength of 640 nm. When the length of a covalent bond of π electrons of polydiacetylene is decreased by heat, pH, physical or chemical stimuli or molecular recognition, the color thereof is changed from blue to red, thus revealing a self fluorescence. The radial porous diacetylene particle of the present invention has optical characteristics of color transition and fluorescence-emitting through this mechanism.

Here, the diamine or dicarboxylic acid monomer represented by Formula 2 may include a benzene ring. More preferably, this diamine or dicarboxylic acid monomer may be represented by Formula 3 below:

$$Q\text{-}(H_2C)_m\text{---}C_6H_4\text{---}(CH_2)_n\text{-}Q \quad \text{[Formula 3]}$$

wherein Q is selected from COOH and $NH_2$, and m and n are each independently an integer of 1 to 10.

The radial porous diacetylene particle of the present invention is synthesized by ion-bonding the diacetylene-containing dicarboxylic acid or diamine monomer represented by Formula 1 above with the diamine or dicarboxylic acid monomer represented by Formula 2 above to form a radial porous diacetylene particle and then growing the radial porous diacetylene particle. Concretely, a carboxylic acid group was radially ion-bonded with an amine group, so that radial porous diacetylene particles having specific porosity are formed and grown by interactions such as the Van der Waal's force between carbon chains and the π-π bond between benzene rings, respectively.

The radial porous diacetylene particle of the present invention is ion-bonded and grown to form pores having a large surface area.

The particle size of the radial porous diacetylene particle is 50 nm~50 μm, preferably, 1 μm~10 μm.

The pore size of the radial porous diacetylene particle is 1 nm~1 μm, preferably, 2 nm~100 nm.

The present invention provides a method of manufacturing a radial porous diacetylene particle, comprising the steps of:

(a) respectively dissolving a diacetylene-containing dicarboxylic acid or diamine monomer represented by Formula 1 below and a diamine or dicarboxylic acid monomer represented by Formula 2 below in a solvent to prepare a solution including the diacetylene-containing dicarboxylic acid or diamine monomer and a solution including the diamine or dicarboxylic acid monomer:

$$G\text{-}(A)_x\text{-}C\equiv C\text{---}C\equiv C\text{---}(B)_y\text{-}G \quad \text{[Formula 1]}$$

wherein A and B are each independently selected from a substituted or unsubstituted alkyl group of two or more carbon atoms, an ethylene oxide group, an amide group and an ester group, G is selected from COOH and $NH_2$, and x and y are each independently an integer of 1 to 20, $$Q\text{-}(D)_m\text{-}Z\text{-}(E)_n\text{-}Q \quad \text{[Formula 2]}$$

wherein Z is selected from a substituted or unsubstituted alkyl group of one or more carbon atoms, a benzene group, a cycloalkyl group, a pyridine group, a pyrimidine group and a naphthalene group, D and E are each independently selected from a substituted or unsubstituted alkyl group of one or more carbon atoms, a benzene group, a cycloalkyl group, a pyridine group, a pyrimidine group and a naphthalene group, D, E and Z are different from each other, Q is selected from COOH and $NH_2$, m and n are each independently an integer of 0 to 20, and G of Formula 1 above is different from Q of Formula 2 above;

(b) ultrasonically treating each of the solutions;

(c) maintaining each of the ultrasonically-treated solutions at room temperature; and (d) mixing the solution including the diacetylene-containing dicarboxylic acid or diamine monomer represented by Formula 1 above with the solution including the diamine or dicarboxylic acid monomer represented by Formula 2 above to form a radial porous diacetylene particle and then growing the radial porous diacetylene particle.

The solvent used may be selected without limitation if it is generally used in the related field. Preferably, the solvent may be at least one selected from the group consisting of tetrahydrofuran (THF), chloroform, toluene, ethanol, isopropanol, and n-hexane, and more preferably, the solvent may be tetrahydrofuran (THF).

The concentration of the solution including the diacetylene-containing dicarboxylic acid or diamine monomer represented by Formula 1 above may be 10 mM~50 mM, and the concentration of the solution including the diamine or dicarboxylic acid monomer represented by Formula 2 above may be 10 mM~50 mM. More preferably, the concentration of the solution including the diacetylene-containing dicarboxylic acid or diamine monomer represented by Formula 1 above may be 5 mM~10 mM, and the concentration of the solution including the diamine or dicarboxylic acid monomer represented by Formula 2 above may be 5 mM~10 mM.

In step (d), when the solution including the diacetylene-containing dicarboxylic acid or diamine monomer represented by Formula 1 above is mixed with the solution including the diamine or dicarboxylic acid monomer represented by Formula 2 above, it is preferred that the concentrations of these solutions may be equal to each other, but the present invention is not limited thereto.

The ultrasonic treatment may be carried out for 30 minutes by a power of 5~20 W, preferably for 15 minutes by a power of 10~15 W, and more preferably for 10 minutes by a power of 10 W.

In step (c), each of the ultrasonically-treated solutions at room temperature may be maintained at a room temperature of 5~30° C. for 10 minutes~1 hour, preferably at a room temperature of 10~25° C. for 10 minutes~1 hour.

In step (d), the mixing temperature of the solution including the diacetylene-containing dicarboxylic acid or diamine monomer represented by Formula 1 above with the solution including the diamine or dicarboxylic acid monomer represented by Formula 2 above may be 5~30° C., preferably, 10~25° C. When the mixing temperature is lower than 5° C., pores are not easily formed, and when the mixing temperature is higher than 30° C., particles are not easily formed and irregular pores are formed.

It is preferred that the maintaining temperature in step (c) and the mixing temperature in step (d) be equal to each other, but the present invention is not limited thereto.

In step (d), the solution including the diacetylene-containing dicarboxylic acid or diamine monomer represented by Formula 1 above and the solution including the diamine or dicarboxylic acid monomer represented by Formula 2 above may be mixed in a volume ratio of 1:0.2~5, preferably 1:0.5~3, and more preferably 1:1.

The method may further include the step of exposing the radial porous diacetylene particle to UV having a wavelength of 254 nm and applying thermal stimuli thereto to confirm the specific optical characteristics of polydiacetylene.

According to the present invention, the size, porosity and optical characteristics of the radial porous diacetylene particle can be adjusted by adjusting the diacetylene-containing dicarboxylic acid or diamine monomer represented by Formula 1 above and the diamine or dicarboxylic acid monomer represented by Formula 2 above.

The size and porosity of the radial porous diacetylene particle can be adjusted by adjusting the concentration of each of the solutions including the monomers.

The porosity of the radial porous diacetylene particle can be adjusted by adjusting the mixing ratio of the solutions including the monomers.

The size and porosity of the radial porous diacetylene particle can be adjusted by adjusting the mixing temperature of the solutions including the monomers.

Further, the radial porous diacetylene particle can be applied to a chemical sensor, a DNA sensor, a protein sensor or a cell sensor by introducing a receptor into the radial porous diacetylene particles and using optical characteristics.

Hereinafter, the present invention will be described in more detail with reference to the following Examples. These Examples are set forth only to illustrate the present invention, and the scope of the present invention is not limited thereto.

Example 1: Preparation of Monomer Solutions (DCDDA Solution and pXDA Solution)

0.03625 g of DCDDA (10,12-Docosadiynedioic acid) and 0.01362 g of pXDA (p-Xylylene diamine) were respectively dissolved in 10 ml of THF (tetrahydrofuran) in a glass bottle to prepare 10 Mm monomer solutions. Subsequently, each of the monomer solutions was ultrasonically treated for 10 minutes by a power of 10 W using an ultrasonic generator, and was then maintained at 15° C. for 20 minutes.

Example 2: Manufacture of Radial Porous Diacetylene Particle 5 ml of the DCDDA solution and 5 ml of the pXDA solution prepared in Example 1 were mixed at a volume ratio of 1:1 at 15° C. by injecting the DCDDA solution into the pXDA solution using a pipette.

In this case, a carboxylic acid group was radially ion-bonded with an amine group, and thus radial porous diacetylene particles having specific porosity were formed and grown by interaction between carbon chains and between benzene rings, respectively.

Figure 1:
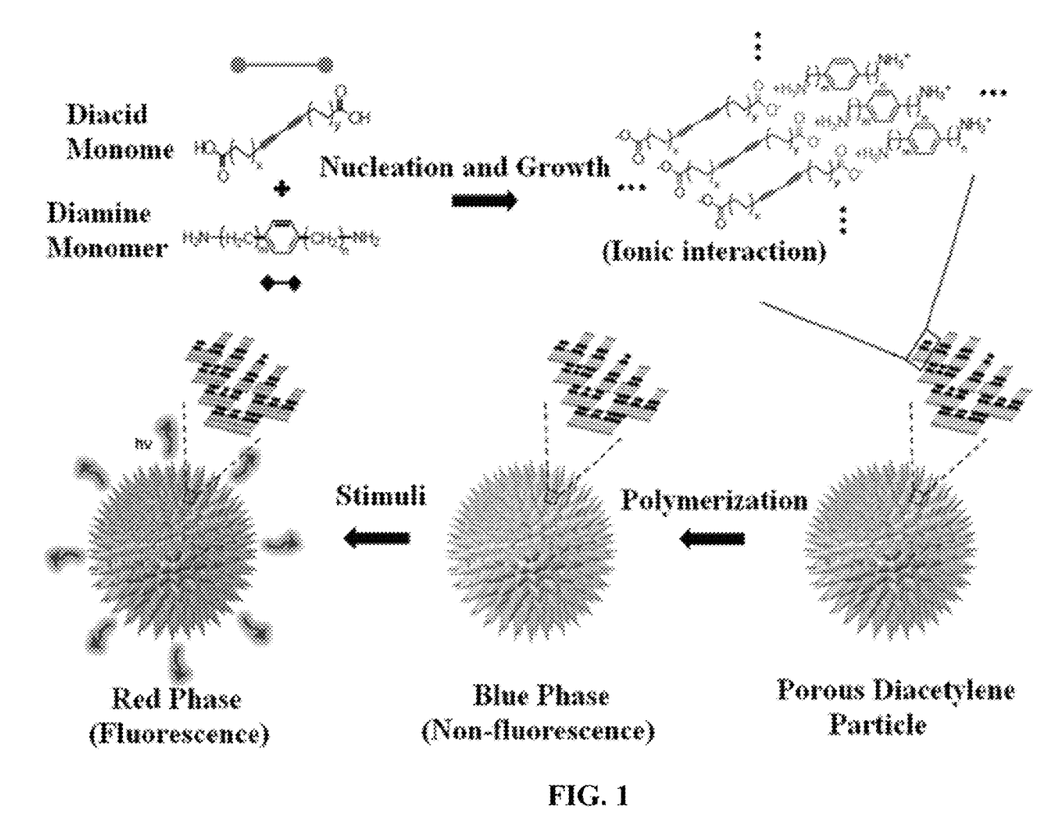
FIG. 1 is a schematic view showing the formation of radial porous diacetylene particles according to the present invention.
Figure 2:
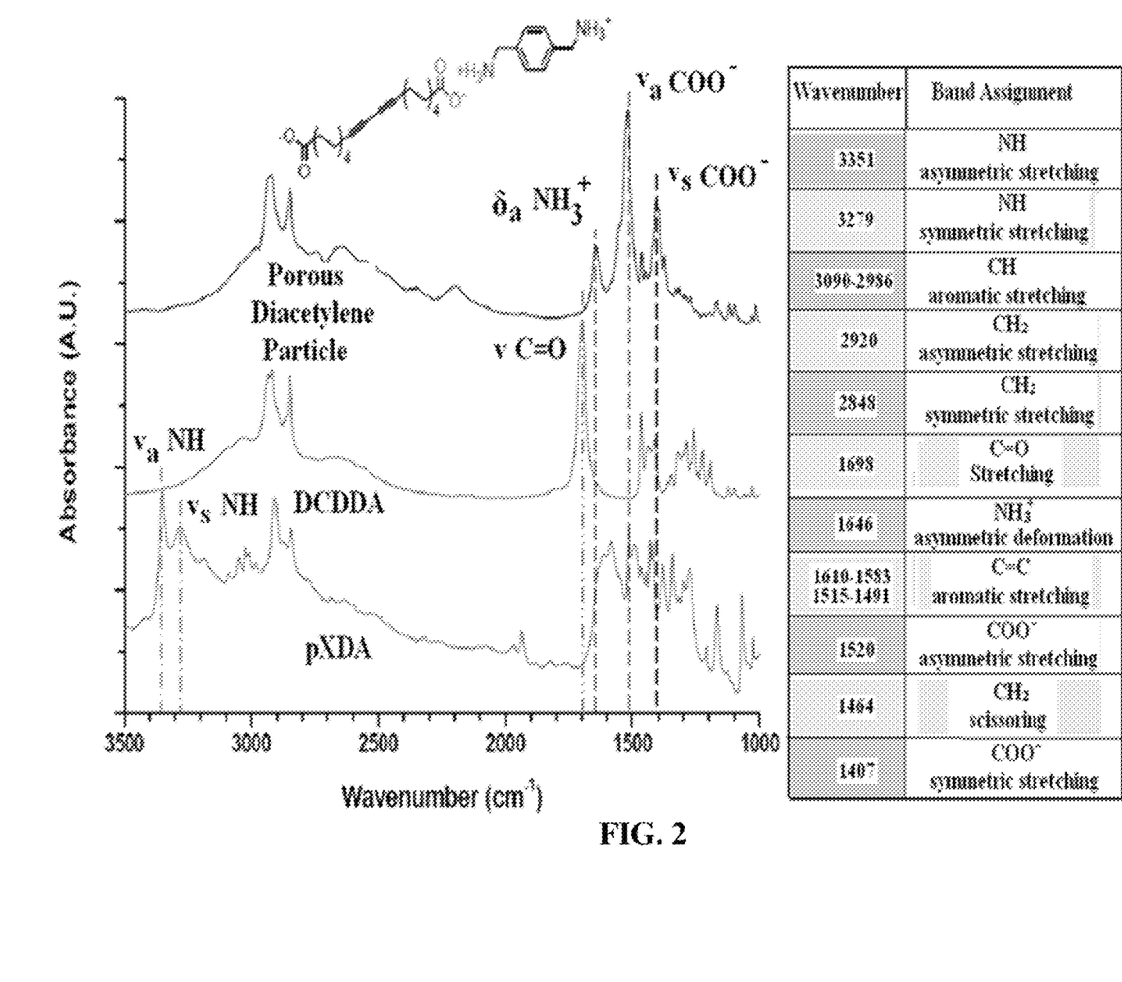
FIG. 2 is a graph showing the results of analyzing the formation mechanism of the radial porous diacetylene particles using FTIR.

FIG. 1 is a schematic view showing the formation of such radial porous diacetylene particles, and FIG. 2 is a graph showing the results of analyzing the formation mechanism of the radial porous diacetylene particles using FTIR.

Figure 3:
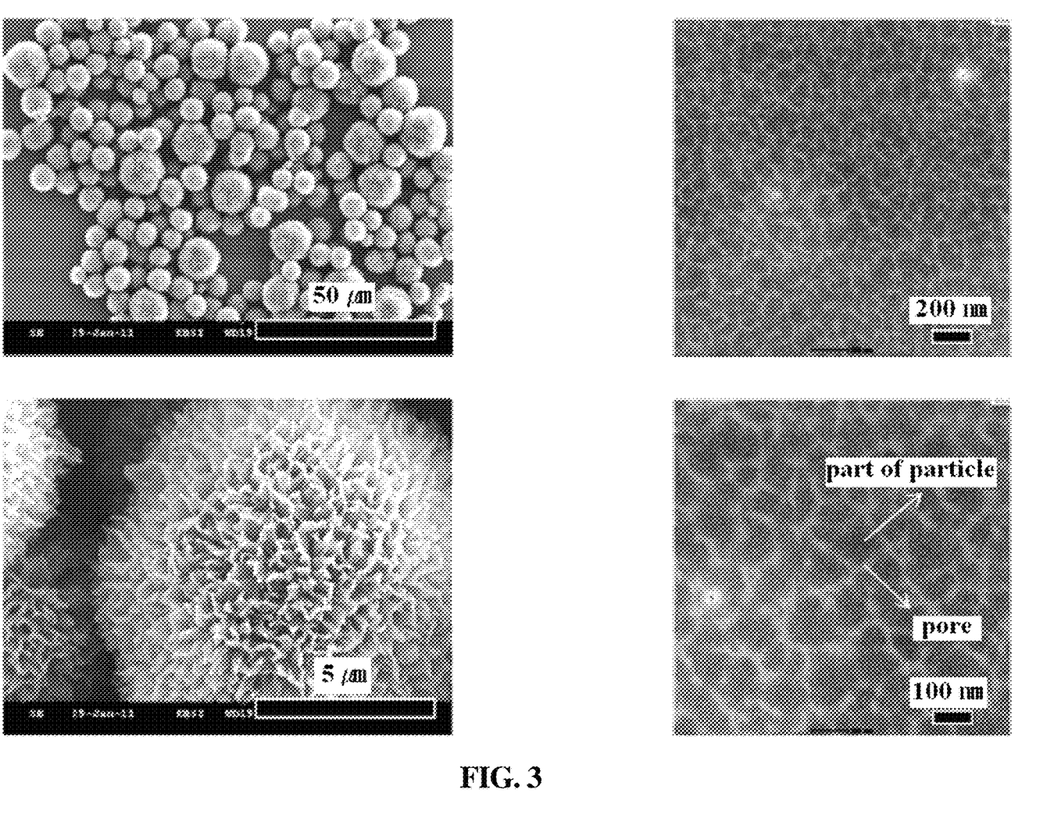
FIG. 3 is photographs showing the surface and inner structure of the radial porous diacetylene particles.

The formed radial porous diacetylene particle has a particle size of 1~10 μm and a pore size of 2~500 nm. The results thereof are shown in FIG. 3 by scanning electron microscope (SEM) photographs (left of FIG. 3) and transmission electron microscope (TEM) photographs (right of FIG. 3).

Example 3: Analysis of Optical Characteristics of Radial Porous Diacetylene Particle Depending on Thermal Stimuli When 4 μl of the radial porous diacetylene particle solution manufactured in Example 2 was dropped onto a silicon or glass substrate and then dried, any color was not realized and fluorescence was not revealed. When the radial porous diacetylene particle was exposed to UV of 254 nm at a rate of 1 mW/cm$^2$, this radial porous diacetylene particle is polymerized, thus revealing blue color and not revealing red fluorescence.

Figure 4:
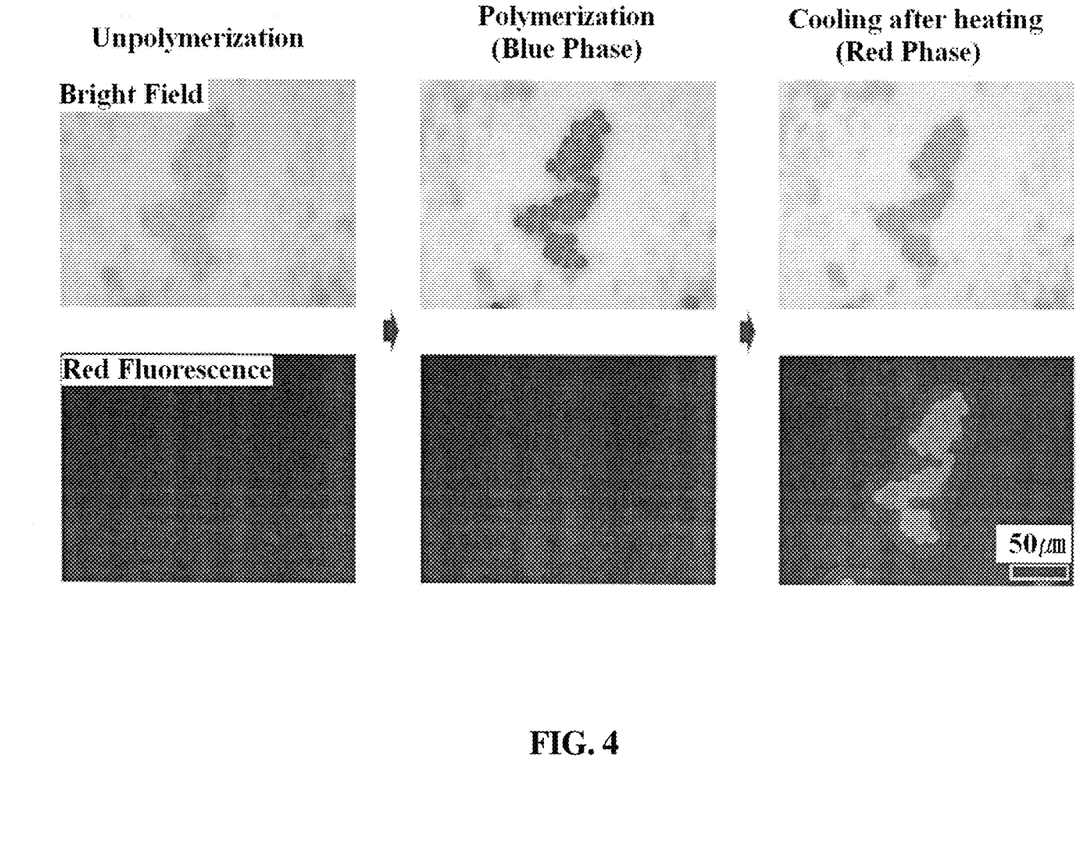
FIG. 4 is photographs showing the change of optical characteristics of the radial porous diacetylene particles depending on the polymerization thereof and the thermal stimuli thereto.

When the radial porous diacetylene particle was heated at 110° C. for 36 hours, it became red, and revealed red fluorescence. The results thereof are shown in FIG. 4.

Figure 5:
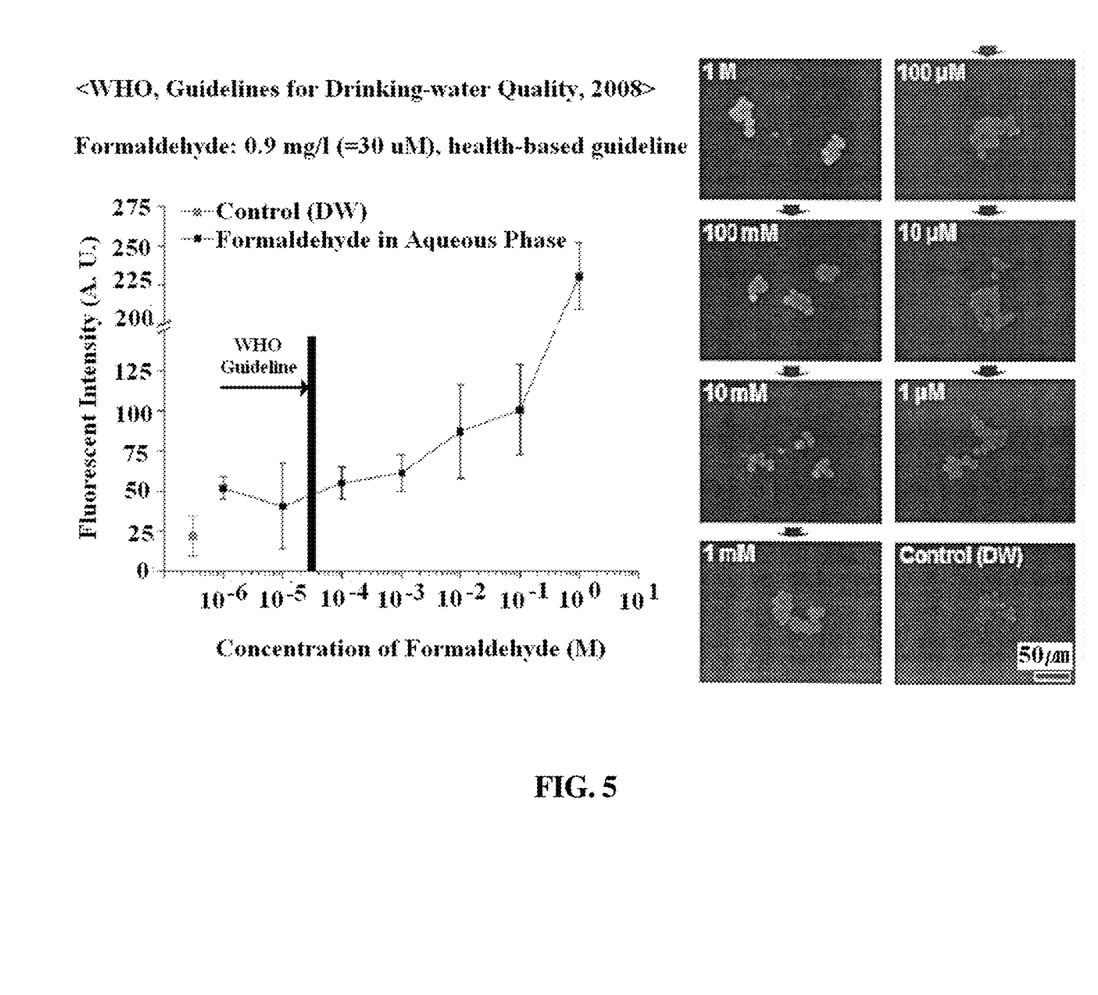
FIG. 5 is a graph showing the fluorescent intensity of the radial porous diacetylene particles relative to the concentration of liquid formaldehyde.

Example 4: Analysis of Fluorescence of Radial Porous Diacetylene Particle Depending on the Concentration of an Aqueous Formaldehyde Solution The polymerized radial porous diacetylene particle of Example 2 was dropped into an aqueous formaldehyde solution to a concentration of 1 M to 1 μM by 200 μM. Then, a reaction was carried out for 2 minutes, the unreacted solution was removed using nitrogen, and then red fluorescence was analyzed. As a result, as shown in FIG. 5, it can be ascertained that the fluorescent intensity of the radial porous diacetylene particle was gradually decreased as the concentration of formaldehyde was decreased.

Example 5: Analysis of Thermal Stability of Radial Porous Diacetylene Particle

Figure 6:
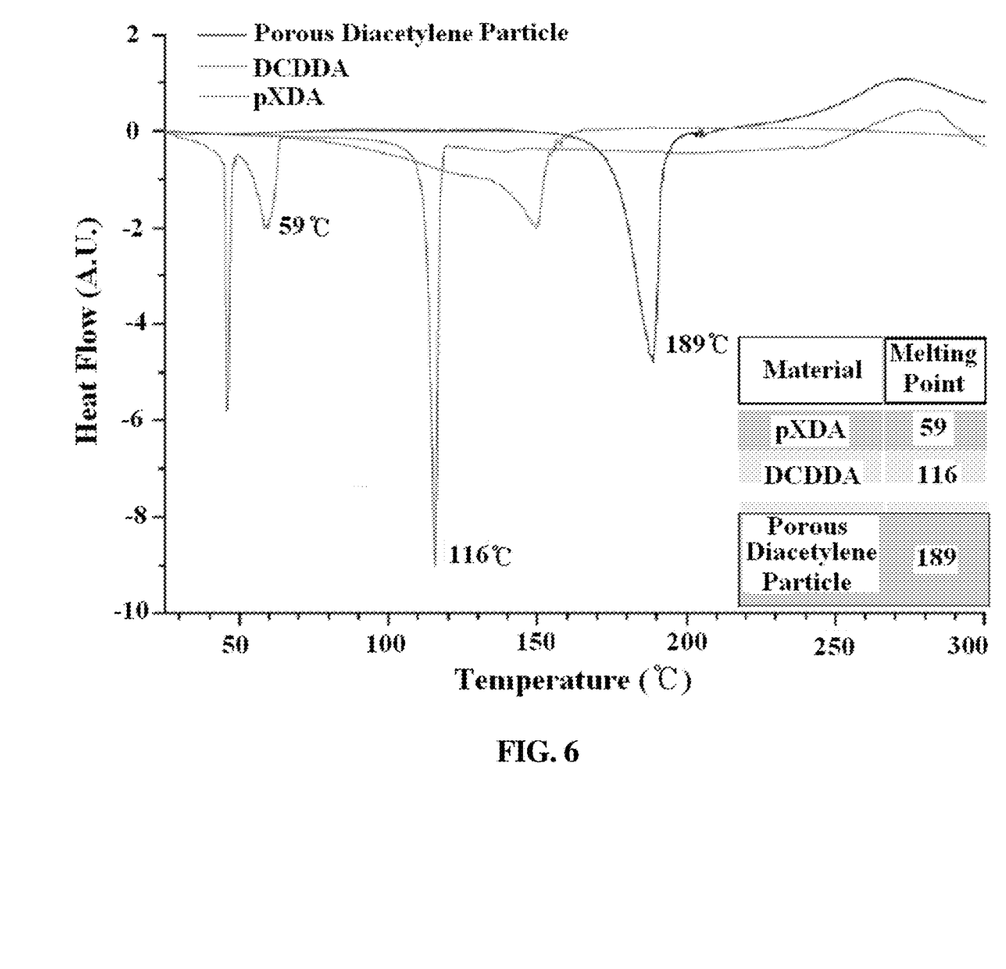
FIG. 6 is a graph showing the results of analyzing the thermal stability of the radial porous diacetylene particles using a differential scanning calorimeter (DSC)

In order to analyze the thermal stability of the radial porous diacetylene particle manufactured in Example 2, the radial porous diacetylene particle was observed using a differential scanning calorimeter (DSC 2010, manufactured by TA Instruments Corp. in U.S.A). The results thereof are shown in FIG. 6. From FIG. 6, it can be ascertained that the radial porous diacetylene particle has excellent thermal stability because its melting point is higher than that of each of the monomers.

Example 6: Analysis of the Changes in Characteristics of Radial Porous Diacetylene Particles Depending on the Concentrations of Monomer Solutions DCDDA (10,12-docosadiynedioic acid) and pXDA (p-xylylene diamine) were respectively dissolved in THF (tetrahydrofuran) to prepare DCDDA solutions having concentrations of 5 mM, 10 mM, 20 mM, 30 mM, 40 mM and 50 mM and pXDA solutions having concentrations of 5 mM, 10 mM, 20 mM, 30 mM, 40 mM and 50 mM. Thereafter, each of the prepared monomer solutions was ultrasonically treated for 10 minutes by a power of 10 W using an ultrasonic generator, and was then maintained at 15° C. for 20 minutes. Subsequently, the DCDDA solution and the pXDA solution having the same concentration were mixed at a volume ratio of 1:1 by injecting the DCDDA solution into the pXDA solution using a micropipette. Thus, carboxylic acid ions of DCDDA were bonded with amine ions of pXDA to form and grow radial porous diacetylene particles.

Figure 7:
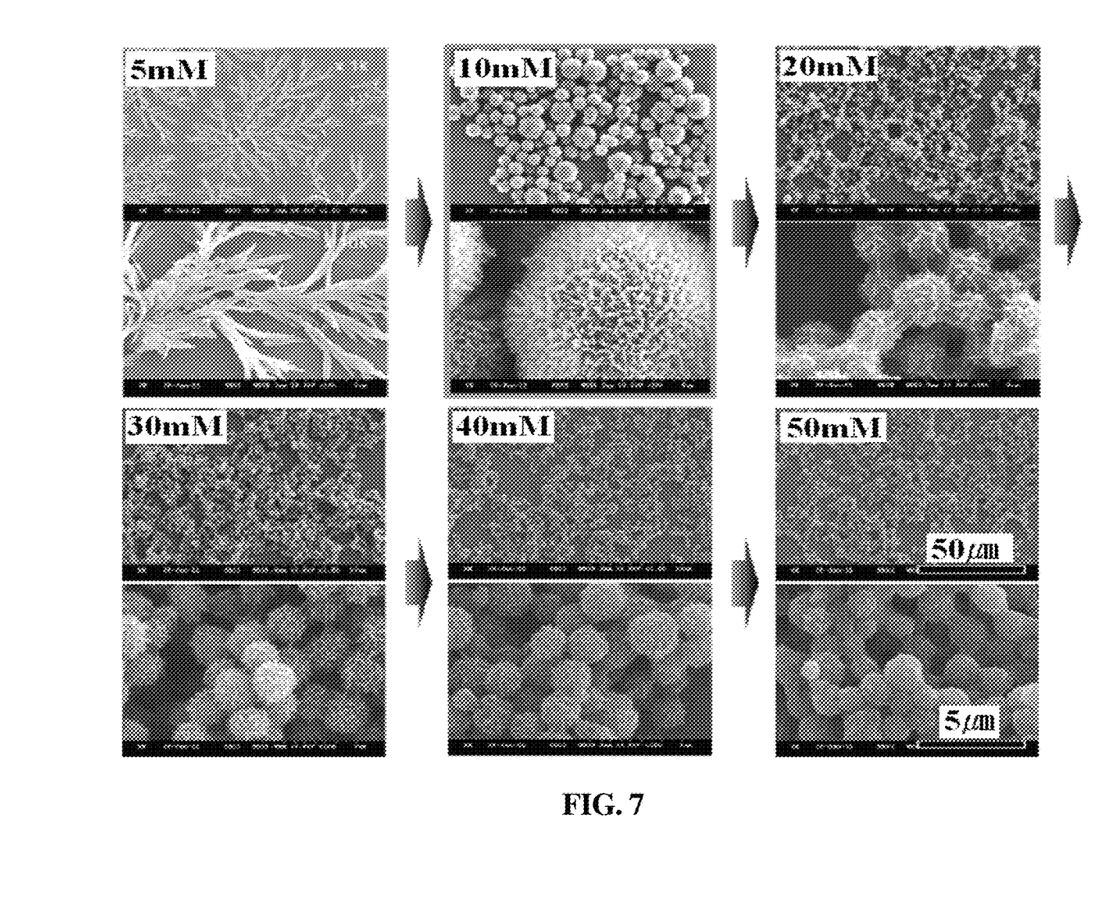
FIG. 7 is photographs showing the results of analyzing the surface structure of the radial porous diacetylene particles according to the concentration of a dicarboxylic acid monomer solution and the concentration of a diamine monomer solution.

The size and porosity of the radial porous diacetylene particles formed depending on the concentration of each monomer solution were measured using a scanning electron microscope (SEM) and then observed. The results thereof are shown in FIG. 7. As shown in FIG. 7, it can be ascertained that radial porous diacetylene particles were not easily formed when the concentration of each monomer solution was less than 5 mM, and that radial porous diacetylene particles were formed but the porosity thereof was low when the concentration of each monomer solution was more than 20 mM.

Example 7: Analysis of the Changes in Characteristics of Radial Porous Diacetylene Particles Depending on the Mixing Monomer Solutions In order to observe the porosity of radial porous diacetylene particles depending on the mixing ratio of a DCDDA solution and a pXDA solution, the DCDDA solution and pXDA solutions prepared in Example 1 were respectively mixed at mixing ratios of 1:3, 1:2, 1:1, 2:1 and 3:1. In this case, the DCDDA solution and the pXDA solution were mixed by injecting the DCDDA solution into the pXDA solution using a micropipette to form and grow radial porous diacetylene particles.

Figure 8:
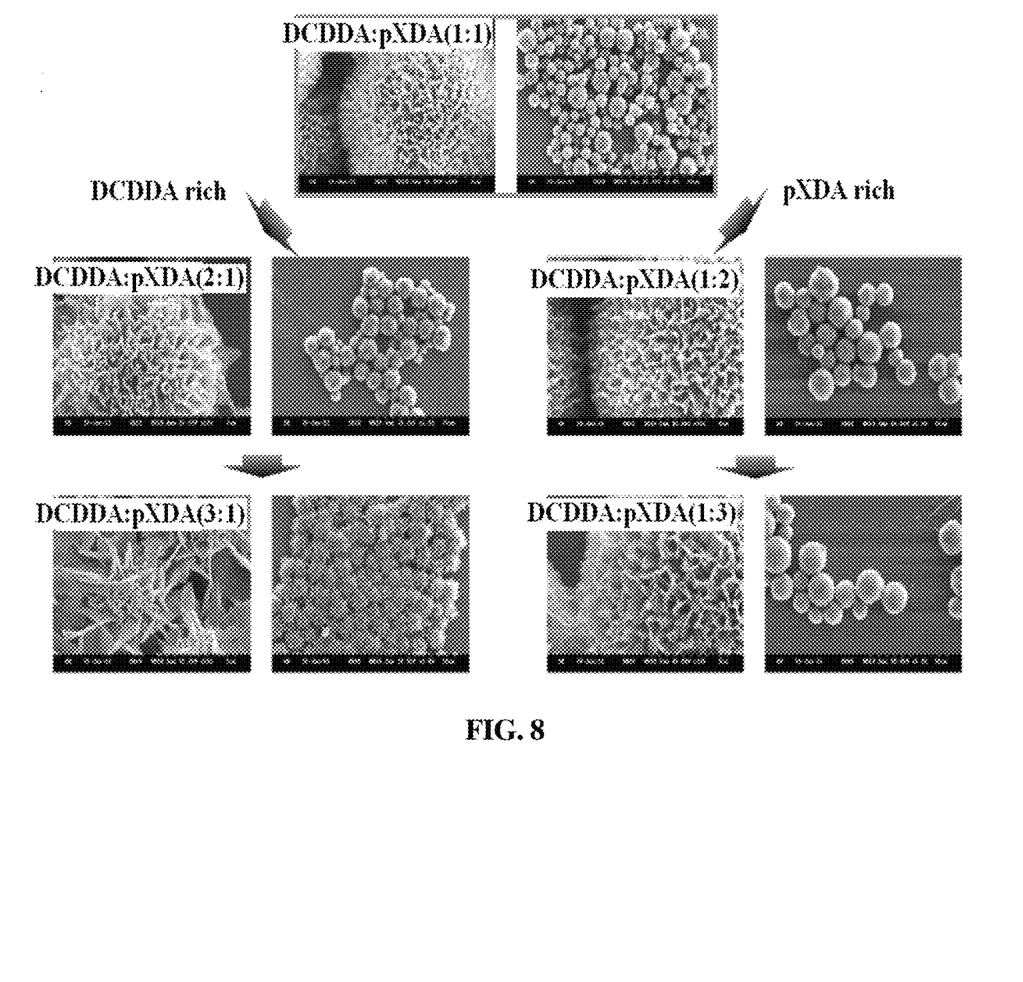
FIG. 8 is photographs showing the results of analyzing the surface structure of the radial porous diacetylene particles according to the mixing ratio of a dicarboxylic acid monomer solution and a diamine monomer solution.

The radial porous diacetylene particles formed by using different mixing ratios of the monomer solutions were measured using a scanning electron microscope (SEM) and then observed. The results thereof are shown in FIG. 8. As shown in FIG. 8, it can be ascertained that the pore size of radial porous diacetylene particles was increased as the ratio of pXDA was increased at the time of mixing, and that the pore sizes thereof became irregular and the pores thereof were not easily formed as the ratio of DCDDA was increased.

Example 8: Analysis of the Changes in Characteristics of Radial Porous Diacetylene Particles Depending on the Mixing Temperature of Monomer Solutions 0.03625 g of DCDDA (10,12-Docosadiynedioic acid) and 0.01362 g of pXDA (p-Xylylene diamine) were respectively dissolved in 10 ml of THF (tetrahydrofuran) in a glass bottle to prepare 10 Mm monomer solutions. Subsequently, each of the monomer solutions was ultrasonically treated for 10 minutes by a power of 10 W using an ultrasonic generator, and was then maintained for 20 minutes at 5, 10, 15, 20, 25 and 30° C., respectively. Subsequently, the DCDDA solution and the pXDA solution were mixed at a volume ratio of 1:1 at 5, 10, 15, 20, 25 and 30° C., respectively. In this case, the DCDDA solution and the pXDA solution were mixed by injecting the DCDDA solution into the pXDA solution using a micropipette to form and grow radial porous diacetylene particles.

The maintenance temperature and mixing temperature were equal to each other.

Figure 9:
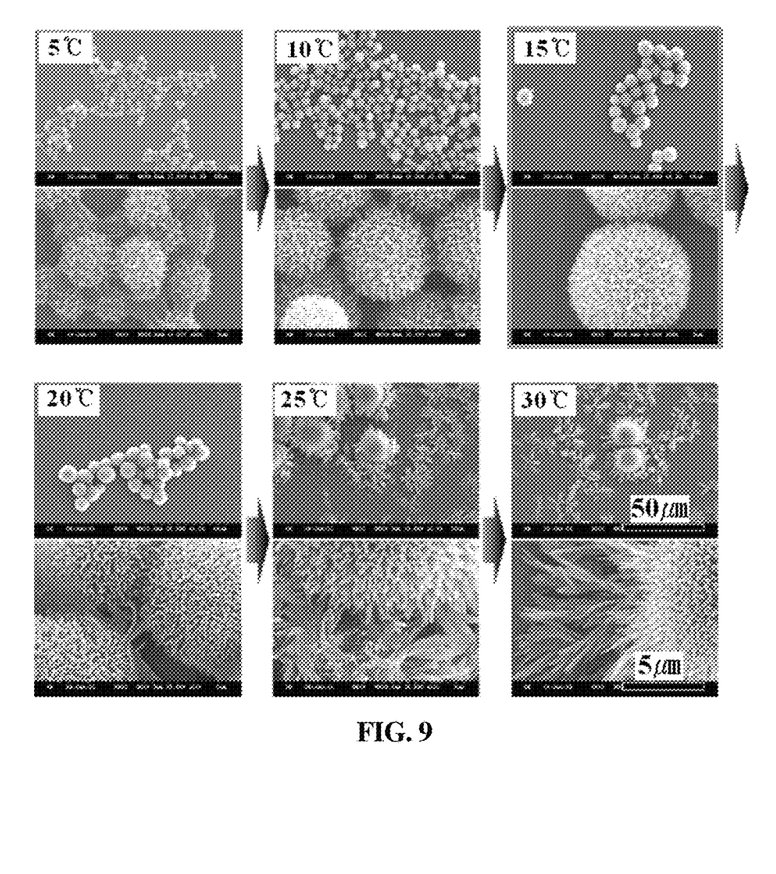
FIG. 9 is photographs showing the results of analyzing the surface structure of the radial porous diacetylene particles according to the temperature when mixing a dicarboxylic acid monomer solution and a diamine monomer solution.

The radial porous diacetylene particles formed depending on the mixing temperature of the monomer solutions were measured using a scanning electron microscope (SEM) and then observed. The results thereof are shown in FIG. 9. As shown in FIG. 9, it can be ascertained that the radial porous diacetylene particles were not easily formed at 30° C. or more, that the radial porous diacetylene particles were not easily formed and the pore sizes thereof became irregular at more than 25° C., and that the pores thereof were not easily formed at less than 10° C.

Example 9: Analysis of the Changes in Characteristics of Radial Porous Diacetylene Particles Depending on Whether or not a Carboxylic Acid Group, an Amine Group, a Diacetylene Group or a Benzene Group was Used DCDDA (10,12-Docosadiynedioic acid) having two carboxylic acid groups and a diacetylene group, TCDA (10,12-Tricosadiynoic acid) having one carboxylic acid group and a diacetylene group, DCDA (Docosanedioic acid) having two carboxylic acid group, pXDA (p-Xylylene diamine) having two amine groups and a benzene group, HMDA (Hexamethylenediamine) having two amine groups, EBA (4-Ethyl-benzylamine) having one amine group and a benzene group and DEB (1,4-Diethyl-benzene) having a benzene group were respectively dissolved in THF (Tetrahydrofuran) to prepare 10 mM monomer solutions. Thereafter, the prepared monomer solutions were treated for 10 minutes by a power of 10 W, and were then maintained at 15° C. for 20 minutes. Each of the DCDDA, TCDA and DCDA solutions was mixed with the pXDA solution at a volume ratio of 1:1 by injecting each of the solutions into the pXDA solution using a micropipette. Further, each of the HMDA, EBA and DEB solutions was mixed with the DCDDA solution at a volume ratio of 1:1 by injecting each of the solutions into the DCDDA solution using a micropipette.

Figure 10:
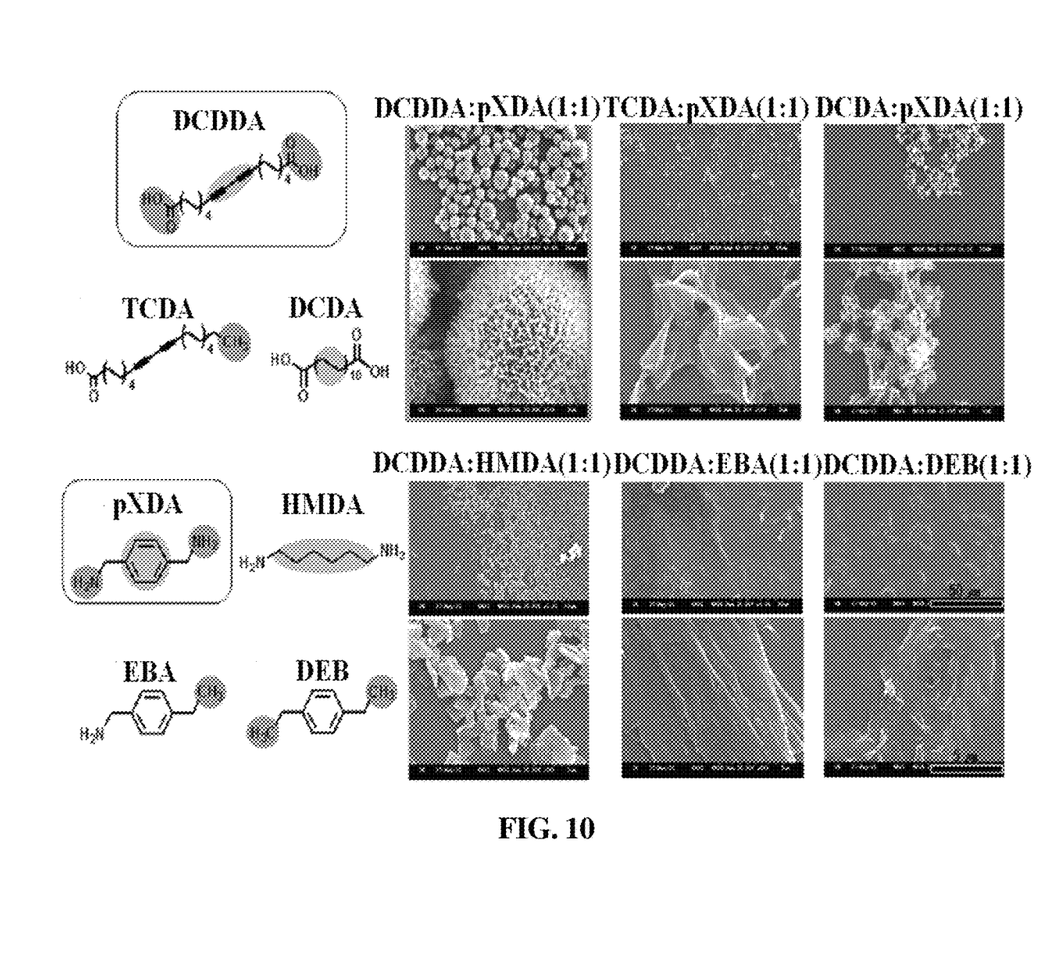
FIG. 10 is photographs showing the results of analyzing the surface structure of the radial porous diacetylene particles according to the existence and nonexistence of a carboxylic acid group, an amine group, a diacetylene group or a benzene group.

The radial porous diacetylene particles formed in this way were measured using a scanning electron microscope (SEM) and then observed. The results thereof are shown in FIG. 10. As shown in FIG. 10, it can be ascertained that radial porous diacetylene particles were formed only when DCDDA having two carboxylic acid groups and a diacetylene group and PXDA having two amine groups and a benzene group were used.

As described above, the radial porous diacetylene particle according to the present invention can easily detect chemical and biological materials harmful to the human body for a short period of time and has very high fluorescent intensity because it has pores having a higher surface area than that of a conventional polydiacetylene sensor. Since a conventional polydiacetylene sensor is sensitive to thermal stimuli, it must be carefully treated. However, since the radial porous diacetylene particle of the present invention is not sensitive to thermal stimuli, it can be easily treated at room temperature.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method of manufacturing a radial porous diacetylene particle, comprising the steps of:
   (a) respectively dissolving a diacetylene-containing dicarboxylic acid monomer represented by Formula 1 below and a diamine monomer represented by Formula 2 below in a solvent to prepare a solution including the diacetylene-containing dicarboxylic acid monomer and a solution including the diamine monomer:

$$G\text{-}(A)_x\text{-}C\equiv C\text{—}C\equiv C\text{—}(B)_y\text{-}G \quad \text{[Formula 1]}$$

wherein A and B are each independently selected from the group consisting of a substituted or unsubstituted alkyl group of two or more carbon atoms, an ethylene oxide group, an amide group and an ester group, G is COOH, and x and y are each independently an integer of 1 to 20, $$Q\text{-}(D)_m\text{-}Z\text{-}(E)_n\text{-}Q \quad \text{[Formula 2]}$$

wherein Z is selected from the group consisting of a benzene group, a pyridine group, a pyrimidine group and a naphthalene group, D and E are each independently a substituted or unsubstituted alkyl group of one or more carbon atoms Q, $NH_2$, and m and n are each independently an integer of 0 to 20;
   (b) ultrasonically treating each of the solutions;
   (c) maintaining each of the ultrasonically-treated solutions at room temperature; and
   (d) mixing the solution including the diacetylene-containing dicarboxylic acid monomer represented by Formula 1 above with the solution including the diamine monomer represented by Formula 2 above to form a radial porous diacetylene particle and then growing the radial porous acetylene particle.

2. The method according to claim 1, wherein the solvent is at least one selected from the group consisting of tetrahydrofuran (THF), chloroform, toluene, ethanol, isopropanol, and n-hexane.

3. The method according to claim 1, wherein each of the solution including the diacetylene-containing dicarboxylic acid monomer represented by Formula 1 above and the solution including the diamine monomer represented by Formula 2 above has a concentration of 10 mM~50 mM.

4. The method according to claim 1, wherein each of the solution including the diacetylene-containing dicarboxylic acid monomer represented by Formula 1 above and the solution including the diamine monomer represented by Formula 2 above has a concentration of 10 mM~20 mM.

5. The method according to claim 1, wherein a mixing temperature of the step (d) is maintained at a temperature of 5~30° C. for 10 minutes~1 hour.

6. The method according to claim 1, wherein a mixing temperature of the step (d) is maintained at a temperature of 10~25° C. for 10 minutes~1 hour.

7. The method according to claim 1, wherein the solution including the diacetylene-containing dicarboxylic acid monomer represented by Formula 1 above and the solution including the diamine monomer represented by Formula 2 above are mixed in a volume ratio of 1:0.2~5.

8. The method according to claim 1, wherein the ultrasonic treatment is carried out for 30 minutes by a power of 5~20 W.

* * * * *